United States Patent
Xu

(10) Patent No.: US 6,777,223 B2
(45) Date of Patent: Aug. 17, 2004

(54) METHODS FOR ELIMINATING THE FORMATION OF BIOFILM

(75) Inventor: Feng Xu, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/885,379

(22) Filed: Jun. 19, 2001

(65) Prior Publication Data

US 2004/0109852 A1 Jun. 10, 2004

Related U.S. Application Data

(63) Continuation-in-part of application No. 09/596,795, filed on Jun. 19, 2000.
(51) Int. Cl.[7] .............................. C12S 9/00; A61K 38/43
(52) U.S. Cl. .................... 435/262.5; 435/189; 435/190; 424/94.2; 424/94.1; 210/632
(58) Field of Search .............................. 435/262.5, 189, 435/190; 424/94.2, 94.1; 210/632

(56) References Cited

U.S. PATENT DOCUMENTS 4,936,994 A * 6/1990 Wiatr .......................... 210/632
5,411,666 A * 5/1995 Hollis et al. ................. 210/632

FOREIGN PATENT DOCUMENTS

| WO | WO 98/58075 | 12/1998 |
| WO | WO 00/28043 | * 5/2000 |

OTHER PUBLICATIONS

Allison et al., FEMS Microbiol., Lett. 1998, 167(2), 179–184.*
Costerton et al., 1999, Science 284: 1318–1322.
Davies et al., 1998, Science 280: 295–298.

* cited by examiner

Primary Examiner—Irene Marx
(74) Attorney, Agent, or Firm—Robert L. Starnes

(57) ABSTRACT

The present invention relates to methods for preventing or removing biofilm on a surface, comprising contacting the surface with an effective amount of a composition comprising one or more acylases and a carrier to degrade a lactone produced by one or more microorganisms, wherein the degradation of the lactone prevents or removes the biofilm.

29 Claims, 2 Drawing Sheets

METHODS FOR ELIMINATING THE FORMATION OF BIOFILM

CROSS-REFERENCE TO RELATED APPLICATION

This application is a continuation-in-part of pending U.S. application Ser. No. 09/596,795 filed Jun. 19, 2000, which application is fully incorporated herein by reference.

BACKGROUND OF THE INVENTION

1. Field of the Invention

The present invention relates to methods for preventing or removing biofilm on a surface.

2. Description of the Related Art

Biofilms are biological films that develop and persist at the surfaces of biotic or abiotic objects in aqueous environments from the adsorption of microbial cells onto the solid surfaces. This adsorption can provide a competitive advantage for the microorganisms since they can reproduce, are accessible to a wider variety of nutrients and oxygen conditions, are not washed away, and are less sensitive to antimicrobial agents. The formation of the biofilm is also accompanied by the production of exo-polymeric materials (polysaccharides, polyuronic acids, alginates, glycoproteins, and proteins) which together with the cells form thick layers of differentiated structures separated by water-filled spaces. The resident microorganisms may be individual species of microbial cells or mixed communities of microbial cells, which may include aerobic and anaerobic bacteria, algae, protozoa, and fungi. Thus, the biofilm is a complex assembly of living microorganisms embedded in an organic structure composed of one or more matrix polymers which are secreted by the resident microorganisms.

Biofilms can develop into macroscopic structures several millimeters or centimeters in thickness and cover large surface areas. For non-living objects, these formations can play a role in restricting or entirely blocking flow in plumbing systems, decreasing heat transfer in heat exchangers, or causing pathogenic problems in municipal water supplies, food processing, medical devices (e.g., catheters, orthopedic devices, implants). Moreover, biofilms often decrease the life of materials through corrosive action mediated by the embedded microorganisms. This biological fouling is a serious economic problem in industrial water process systems, pulp and paper production processes, cooling water systems, injection wells for oil recovery, cooling towers, porous media (sand and soil), marine environments, and air conditioning systems, and any closed water recirculation system. Biofilms are also a severe problem in medical science and industry causing dental plaque, infections (Costerton et al., 1999, *Science* 284: 1318–1322), contaminated endoscopes and contact lenses, prosthetic device colonisation and biofilm formation on medical implants.

The removal or prevention of biofilm traditionally requires the use of dispersants, surfactants, detergents, enzyme formulations, anti-microbials, biocides, boil-out procedures, and/or corrosive chemicals, e.g., base. Procedures for using these measures are well known in the art. For example, removal of biofilm build-up in a paper machine in the pulp and paper industry traditionally requires a deposit control program including proper housekeeping to keep surfaces free of splashed stock, anti-microbial treatment of fresh water and additives, the use of biocides to reduce microbiological growth on the machine, and scheduled boil-outs to remove the deposits that do form.

Bacteria growing in biofilms are more resistant to antibiotics and disinfectants than planktonic cells and the resistance increases with the age of the biofilm. Bacterial biofilm also exhibits increased physical resistance towards desiccation, extreme temperatures or light. As mentioned, biofilm formation causes industrial, environmental and medical problems and the difficulties in cleaning and disinfection of bacterial biofilm with chemicals is a major concern in many industries. Furthermore, the trend towards milder disinfection and cleaning compositions may increase the insufficient cleaning of surfaces covered with biofilm.

The formation of a biofilm by *Pseudomonas aeruginosa* involves the production of at least two extracellular signals involved in cell-to cell communication (WO 98/58075). The two cell-to-cell signaling systems are the lasR-lasI and rhlR-rhiI (also called vsmR-vsmI) systems (Davies et al., 1998, *Science* 280: 295–298). The lasI gene directs the synthesis of a diffusible extracellular signal, N-(3-oxododecanoyl)-L-homoserine lactone. The lasRproduct is a transcriptional regulator that requires sufficient levels of N-(3-oxododecanoyl)-L-homoserine lactone to activate a number of virulence genes, including lasI, and the rhlR-rhlI system. The rhiI gene directs the synthesis of the extracellular signal, N-buytryl-L-homoserine lactone, which is required for activation of virulence genes and expression of the stationary-phase factor, RpoS, by the rhlR gene product. This type of gene regulation has been termed quorum sensing and response. Davies et al. have demonstrated that the lasR-lasI system is involved in the differentiation of biofilm formation. WO 98/58075 provides a method whereby cell-cell communication in bacteria via the lasR-lasI system is manipulated to control biofilm architecture and structural integrity.

It is an object of the present invention to provide improved methods for preventing or removing biofilm present on a surface.

SUMMARY OF THE INVENTION

The present invention relates to methods for preventing or removing biofilm on a surface, comprising contacting the surface with an effective amount of a composition comprising one or more acylases and a carrier to degrade a lactone produced by one or more microorganisms, wherein the degradation of the lactone prevents or removes the biofilm.

DETAILED DESCRIPTION OF THE INVENTION

Figure 1:
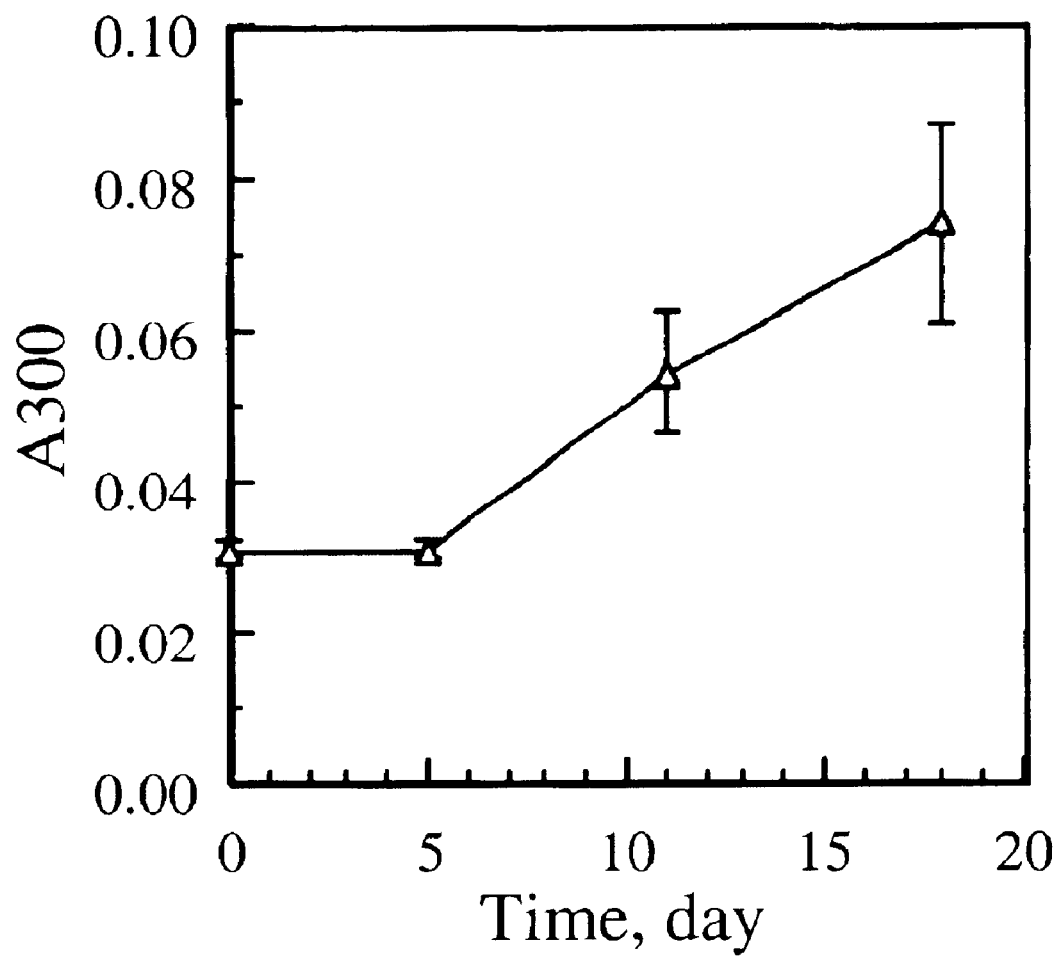
FIG. 1 shows microbial growth-caused absorption change at 300 nm as function of incubation time in the absence of added acylase to fish-tank water sample.

The present invention relates to methods for preventing, removing, or reducing biofilm on a surface, comprising contacting the surface with an effective amount of a composition comprising one or more acylases and a carrier to degrade a lactone produced by one or more microorganisms, wherein the degradation of the lactone prevents, removes, or reduces the biofilm. The methods of the present invention may be used to prevent, remove, reduce, or disrupt biofilm formation on a surface. One of ordinary skill in the art will recognize that such methods may be employed at different stages of biofim formation.

In a preferred embodiment, surfaces prone to biofilm formation may be subjected to the methods of the present invention as a preventative measure prior to any biofilm formation so no biofilm forms. Alternatively, at the first indication of biofim formation, the methods may be used to prevent further formation and to remove the biofim that has deposited on a surface. Furthermore, in situations where there is a heavy build-up of biofilm on a surface, the methods may be used to reduce the level of biofilm or to remove it partially or completely.

A biofilm may comprise an integrated community of one or two or more microorganisms or predominantly a specific microorganism (Palmer and White, 1997, *Trends in Microbiology* 5: 435–440; Costerton et al., 1987, *Annual Reviews of Microbiology* 41: 435–464; Mueller, 1994, *TAPPI Proceedings*, 1994 Biological Sciences Symposium 195–201). In the methods of the present invention, the one or more microorganisms may be any microorganism involved in biofilm formation including, but not limited to, aerobic bacteria or anaerobic bacteria (Gram positive and Gram negative), fungi (yeast or filamentous fungus), to algae, and/or protozoa.

In a preferred embodiment, the microorganism is an aerobic bacterium In a more preferred embodiment, the aerobic bacterium is an Aeromonas strain. In another more preferred embodiment, the aerobic bacterium is a Burkholderie strain. In another more preferred embodiment, the aerobic bacterium is a Flavobacterium strain. In another more preferred embodiment, the aerobic bacterium is a Microbacterium strain. In another more preferred embodiment, the aerobic bacterium is a Pseudomonas strain. In another more preferred embodiment, the aerobic bacterium is a Salmonella strain. In another more preferred embodiment, the aerobic bacterium is a Staphylococcus strain. In another more preferred embodiment, the aerobic bacterium is from the family Enterobacteriaceae (including e.g., *Escherichia coli*).

In a most preferred embodiment, the aerobic bacterium is Burkholderie cepacia. In another most preferred embodiment, the aerobic bacterium is a Microbacterium imperiale. In another most preferred embodiment, the aerobic bacterium is *Pseudomonas aeruginosa*. In another most preferred embodiment, the aerobic bacterium is *Pseudomonas fluorescens*. In another most preferred embodiment, the aerobic bacterium is *Pseudomonas oleovorans* In another most preferred embodiment, the aerobic bacterium is *Pseudomonas pseudoalcaligenes*. In another most preferred embodiment, the aerobic bacterium is *Salmonella enteritidis*. In another most preferred embodiment, the aerobic bacterium is *Staphylococcus aureus*. In another most preferred embodiment, the aerobic bacterium is *Staphylococcus epidermidis*.

In another preferred embodiment, the microorganism is an anaerobic bacteria. In another more preferred embodiment, the anaerobic bacterium is a Desulfovibrio strain. In another most preferred embodiment, the anaerobic bacterium is *Desulfovibrio desulfuricans*.

In another preferred embodiment, the microorganism is a fungus such as a yeast or filamentous fungus. In another more preferred embodiment, the yeast is a Candida strain. In another most preferred embodiment, the yeast is Candida albicans.

The term "surface" is defined herein as any surface which may be covered by biofilm or is prone to biofilm formation. Examples of surfaces may be any hard surface such as metal, plastics, rubber, board, glass, wood, paper, concrete, rock, marble, gypsum and ceramic materials, which optionally are coated, for example, with paint or enamel; any soft surface such as fibers of any kind (e.g., yams, textiles, vegetable fibers, rock wool, and hair); or any porous surfaces; skin (human or animal); keratinous materials (e.g., nails); and internal organs (e.g., lungs). The hard surface can be present as a part of a cooling tower, water treatment plant, water tanks, dairy, food processing plant, chemical or pharmaceutical process plant, or medical device (e.g., catheters, orthopedic devices, implants). The porous surface can be present in a filter, e.g., a membrane filter.

The lactone may be any lactone involved in biofilm formation by a microorganism. In a preferred embodiment, the lactone is a homoserine lactone. In a more preferred embodiment, the lactone is N-acyl-L-homoserine lactone. In a most preferred embodiment, the lactone is N-(3-oxododecanoyl)-L-homoserine lactone. In another most preferred embodiment, the lactone is N-butyryl-L-homoserine lactone.

The term "acylase" is defined herein as a hydrolytic activity which catalyzes the deacylation of N-acylated amino acids or amines. For purposes of the present invention, acylase activity is determined according to the procedure described by Henseling and Rohm, 1988, *Biochimca Biophysica Acta* 959: 370–377, where the release of free amino acid from N-acylated derivatives of amino acids or amines, under the catalysis of the acylase, is monitored photometrically at 340 nm after derivatizing the amine group with o-phthaladehyde in the presence of beta-mercaptoethanol. One unit of acylase activity is defined as 1.0 μmole of L-methionine produced from N-acetyl-L-methionine per minute at 25° C., pH 7. It is understood that the term "acylase" also encompasses aminoacylase, acylaminopeptidase, and acetamidase.

The term "effective amount of one or more acylases" is defined herein as the amount of one or more acylases that is sufficient to degrade a microbially-produced lactone(s) that promotes the formation of biofilm on a surface. The effective amount of the one or more acylases will depend on the acylase(s) and the period of time desirable for degrading a microbially-produced lactone(s). High amounts of the enzyme(s) will likely require shorter times of treatment while low amounts longer times.

In the methods of the present invention, any acylase may be used which possesses suitable enzyme activity in a pH and temperature range appropriate for preventing or removing biofilm. It is preferable that the acylase(s) is active over broad pH and temperature ranges.

In a preferred embodiment, the acylase(s) has a pH optimum in the range of about 3 to about 10. In a more preferred embodiment, the acylase(s) has a pH optimum in the range of about 4 to about 9. In a most preferred embodiment, the acylase(s) has a pH optimum in the range of about 5 to about 8.

In another preferred embodiment, the acylase(s) has a temperature optimum in the range of about 5° C. to about 100° C. In a more preferred embodiment, the acylase(s) has a temperature optimum in the range of about 25° C. to about 75° C. In a most preferred embodiment, the acylase(s) has a temperature optimum in the range of about 25° C. to about 50° C.

In a preferred embodiment, the one or more acylases require $Zn^{2+}$ or other metal ions, are cofactor-independent, are autoproteolysis resistant, and/or are surfactant-tolerant.

The source of the acylase(s) is not critical for use in the methods of the present invention. Accordingly, the acylase (s) may be obtained from any source such as a plant, microorganism, or animal. The acylase(s) is preferably obtained from, e.g., a microbial source, such as a bacterium or a fungus, e.g., a filamentous fungus or a yeast.

In a preferred embodiment, the acylase(s) is obtained from a bacterial source. For example, the acylase(s) may be obtained from an Acetobacter, Acinetobacter, Agrobacterium, Alcaligenes, Arthrobacter, Azotobacter, Bacillus, Comamonas, Clostridium, Gluconobacter, Halobacterium, Mycobacterium, Rhizobium, Salmonella, Serratia, Streptomyces, *E. coli*, Pseudomonas, Wolinella, or methylotrophic bacterium strain.

In a more preferred embodiment, the acylase(s) is obtained from an *Acetobacter aceti, Alcaligenes faecalis, Arthrobacter oxidans, Azotobacter vinelandii, Bacillus alkalophilus, Bacillus amyloliquefaciens, Bacillus anitratum, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis, Comamonas testosteroni, Clostridum tyrobutyricum, Gluconobacter dioxyaceticus, Gluconobacter liquefaciens, Gluconobacter suboxydans, Halobacterium cutirubrum, Mycobacterium convolutum, Rhizobium melioti, Salmonella typhimurium, Serratia marcescens, Streptomyces lividans, Streptomyces murinus, Pseudomonas aeruginosa, Pseudomonas fluorescens, Pseudomonas putida,* or *Wolinella succinogens* strain.

In another preferred embodiment, the acylase(s) is obtained from a fungal source. For example, the acylase(s) may be obtained from a yeast strain such as a Candida, Kluyveromyces, Pichia, Saccharomyces, Schizosaccharomyces, or Yarrowia strain; or from a filamentous fungal strain such as an Acremonium, Aspergillus, Aureobasidium, Chrysosporium, Cryptococcus, Filibasidium, Fusarium, Humicola, Magnaporthe, Monitia, Mucor, Myceliophthora, Neocallimastix, Neurospora, Paecilomyces, Penicillium, Phanerochaete, Piromyces, Schizophyllum, Sclerotium, Sporotrichum, Talaromyces, Thermoascus, Thielavia, Tolypocladium, or Trichoderma strain.

In another more preferred embodiment, the acylase(s) is obtained from a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* strain.

In another more preferred embodiment, the acylase(s) is obtained from an *Aspergillus aculeatus, Aspergillus awamori, Aspergillus foetidus, Aspergillus japonicus, Aspergillus nidulans, Aspergillus niger, Aspergillus oryzae, Chrysosporium lignorum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum Fusarium roseum, Fusarium sambucinum, Fusarium sarcochroum, Fusarium sulphureum, Fusarium toruloseun, Fusarium trichothecioides, Fusarium venenatum, Humicola insolens, Humicola lanuginosa, Monilia sitophila, Mucor miehei, Myceliophthora thermophila, Neurospora crassa, Penicillium purpurogenum, Phanerochaete chrysporurn Polyporus pinsitus, Polyporus versicolor, Sclerotium rolfsii, Sporotrichum thermophile, Trichoderma citrinoviride, Trichoderma hamatum, Trichoderma harzianum, Trichoderma koningii, Trichoderma longibrachiatum, Trichoderma polysporum, Trichoderma reesei, Trichoderma saturnisporum,* or *Trichoderma viride* strain.

The acylase(s) may be obtained from an organism in question by any suitable technique, and in particular by use of recombinant DNA techniques known in the art (c.f. Sambrook, J. et al., 1989, *Molecular Cloning, A Laboratory Manual* Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the acylase and recovering the acylase from the culture. The DNA sequence may be of genomic, cDNA, or synthetic origin, or any mixture of these, and may be isolated or synthesized in accordance with methods known in the art. The acylase may also be obtained from its naturally occurring source, such as a plant or organism, or relevant part thereof. Furthermore, the acylase(s) may be obtained from commercial suppliers.

The treatment time for preventing or removing biofilm will depend on the acylase(s), the dosage of the acylase(s), and the level of biofilm on the surface or prone to the area in question, but should preferably be adapted to the time normally used for conventional treatment of biofilm with antibiotics, biocides, bactericides, fungicides, bleaching agents, surfactants, caustic, and/or biopolymer degrading agents Consequently, the dosage of the acylase(s) may be adjusted according to the time period used during conventional treatments. However, where the acylase treatment is a separate step in the processing, the dosage of the acylase(s) used will depend on the time period desired to accomplish the treatment.

In terms of acylase activity, the appropriate dosage of a given acylase for preventing or removing biofilm will depend on the acylase in question and the amount of biofilm on the surface or prone to the area in question. The skilled person may determine a suitable acylase unit dosage on the basis of acylase assays well known in the art that are specific to the acylase activity of interest. For example, see Henseling and Rohm, 1988, supra; D.

Schomburg and M. Salzmann (editors), 1990, Enzyme Handbook, Springer-Verlag, New York; Von Worthington, 1993, *Worthington Enzyme Manual*, Worthington Biochemical Corporation, Freehold, N.J.; and Hans Ulrich Bergmeyer (editor), 1974, *Methods of Enzymatic Analysis*, Verlag Chemie Weinheim, Academic Press, Inc. New York.

The appropriate dosage of a specific acylase or mixture of two or more acylases for treating biofim may be determined using any conventional method known in the art for determining the growth of microorganisms, e.g., crystal violet staining described by Kolter, 1998, *Molecular Microbiology* 28: 449461

In the methods of the present invention, biofilm contaminated or prone areas are preferably treated for at least 1 to 7 days, more preferably at least 1 to 5 days, even more preferably at least 1 to 3 days, and most preferably at least 1 to 2 days, with a corresponding acylase dosage of preferably about 0.001 to about 1 g, more preferably about 0.01 to about 1 g, even more preferably about 0.01 to about 0.5 g, and most preferably about 0.01 to about 0.1 g of acylase per kilogram of water.

The compositions comprising one or more acylases to be used in the methods of the present invention may be in any form suitable for the use in question, e.g., in the form of a dry powder, agglomerated powder, or granulate, in particular a non-dusting granulate, liquid, in particular a stabilized liquid, or protected acylase. Granulates and agglomerated powders may be prepared by conventional methods, e.g., by spraying the acylase(s) onto a carrier in a fluid-bed granulator. The carrier may consist of particulate cores having a suitable particle size. The carrier may be soluble or insoluble, e.g., a salt (such as sodium chloride or sodium sulfate), sugar (such as sucrose or lactose), sugar alcohol (such as sorbitol), or starch. The acylase(s) and/or additional acylases may be contained in slow-release formulations. Methods for preparing slow-release formulations are well known in the art. Liquid acylase preparations may, for instance, be stabilized by adding nutritionally acceptable stabilizers such as a sugar, sugar alcohol, or another polyol, and/or lactic acid or another organic acid according to established methods.

The composition may be augmented with one or more agents for preventing or removing the formation of the biofilm. These agents may include, but are not limited to, dispersants, surfactants, detergents, other enzymes, antimicrobials, and biocides.

In a preferred embodiment, the agent is a surfactant. In a more preferred embodiment, the surfactant is sodium dodecyl sulfate, quaternary ammonium compounds, alkyl pyridinium iodides, Tween 80, Tween, 85, Triton X-100, Brij 56, biological surfactants, rhamnolipid, surfactin, visconsin, or sulfonates.

The formation of biofilm is generally accompanied by the production of exo-polymeric materials (polysaccharides, polyuronic acids, alginates, glycoproteins, and proteins) which together with the cells form thick layers of differentiated structures separated by water-filled spaces (McEldowney and Fletcher, 1986, *Journal of General Microbiology* 132: 513–523; Sutherland, *Surface Carbohydrates of the Prokaryotic Cell*, Academic Press, New York, 1977, pp. 27–96). In the methods of the present invention, the acylase composition may further comprise one or more other enzymes capable of degrading the exo-polymeric materials such as polysaccharides, polyuronic acids, alginates, glycoproteins, and proteins.

In a preferred embodiment, the one or more other enzymes may be selected from the group consisting of an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The other enzyme(s) may be selected according to the properties of the specific biofilm which is to be removed, or a combination of several enzymes having different enzyme activities may be used.

In a preferred embodiment, the other enzyme is selected from the group consisting of 1,2-1,3-α-D-mannan mannohydrolase, 1,3-βD-xylan xylanohydrolase, 1,3-β-D-glucan glucanohydrolase, 1,3(1,3;1,4)-α-D-glucan 3-glucanohydrolase, 1,3(1,3;1,4)-β-D-glucan 3(4)-glucanohydrolase, 1,3–1,4-α-D-glucan 4-glucanohydrolase, 1,4-α-D-glucan glucanehydrolase, 1,4-α-D-glucan glucohydrolase, 1,4-(1,3:1,4)-β-D-glucan 4-glucanohydrolase, 1,4-β-D-glucan glucohydrolase, 1,4-β-D-xylan xylanohydrolase, 1,4-β-D-mannan mannanohydrolase, 1,5-α-L-arabinan 1,5-α-L-arabinanohydrolase, 1,4-α-D-glucan maltohydrolase, 1,6-α-D-glucan 6-glucanohydrolase, 2,6-β-D-fructan fructanohydrolase, α-Dextrin 6-glucanohydrolase, α-D-galactoside galactohydrolase, α-D-glucoside glucohydrolase, α-D-mannoside mannohydrolase, acyineuraminyl hydrolase, Aerobacter-capsular-polysaccharide galactohydrolase, β-D-fructofuranoside fructohydrolase, β-D-fucoside fucohydrolase, β-D-fructan fructohydrolase, β-D-galactoside galactohydrolase, β-D-glucoside glucohydrolase, β-D-glucuronoside, glucuronosohydrolase, β-D-mannoside mannohydrolase, β-N-acetyl-D-hexosaminide N-acetylhexosamino hydrolase, cellulose-sulfate sulfohydrolase, collagenase, dextrin 6-α-D-glucanohydrolase, glycoprotein-phosphatidylinositol phosphatidohydrolase, hyaluronate 4-glycanohydrolase, hyaluronoglucuronidase, pectin pectylhydrolase, peptidoglycan N-acetylmuramoylhydrolase, phosphatidylcholine 2-acylhydrolase, phosphatidylcholine 1-acylhydrolase, poly(1,4-α-D-galacturonide), poly(1,4-(N-acetyl-β-D-glucosaminide))-glycanohydrolase, sucrose α-glucosidase, triacylglycerol acylhydrolase, and triacylglycerol protein-acylhydrolase.

The other enzyme may be any enzyme having proteolytic activity under the actual process conditions. Thus, the enzyme may be a proteolytic enzyme of plant origin, e.g., papain, bromelain, ficin, or of animal origin, e.g., trypsin and chymotrypsin, or of microbial origin, i.e., bacterial, yeast, or filamentous fungal. It is understood that any mixture of various proteolytic enzyme may be applicable in the process of the invention.

In another preferred embodiment, the other enzyme is a proteolytic enzyme such as a serine protease, a metalloprotease, or an aspartate protease.

A sub-group of the serine proteases are commonly designated as subtilisins. A subtilisin is a serine protease produced by Gram-positive bacteria or fungi. The amino acid sequence of a number of subtilisins have been determined, including at least six subtilisins from Bacillus strains, namely, subtilisin 168, subtilisin BPN, subtilisin Carlsberg, subtilisin DY, subtilisin amylosacchariticus, and mesentericopeptidase, one subtilisin from an actinomycetales, thermitase from Thermoactinomyces vulgaris, and one fungal subtilisin, proteinase K from Tritirachium album. A further subgroup of the subtilisins, subtilases, have been recognised more recently. Subtilases are described as highly alkaline subtilisins and comprise enzymes such as subtilisin PB92 (MAXACAL®, Gist-Brocades NV), subtilisin 309 (SAVINASE®, Novozymes A/S), and subtilisin 147 (ESPERASE®, Novozymes A/S).

A "subtilisin variant or mutated subtilisin protease" is defined herein as a subtilisin that has been produced by an organism which is expressing a mutant gene derived from a parent microorganism which possessed an original or parent gene and which produced a corresponding parent enzyme, the parent gene having been mutated in order to produce the mutant gene from which said mutated subtilisin protease is produced when expressed in a suitable host. These mentioned subtilisins and variants thereof constitute a preferred class of proteases which are useful in the method of the invention. An example of a useful subtilisin variant is a variant of subtilisin 309 (SAVINASE®) wherein, in position 195, glycine is substituted by phenylalanine (G195F or $^{195}$Gly to $^{195}$Phe).

Commercially available proteases may be used in the methods of the present invention. Examples of such commercial proteases are ALCALASE® (produced by submerged fermentation of a strain of Bacillus licheniformis), ESPERASE® (produced by submerged fermentation of an alkalophilic species of Bacillus), RENNILASE® (produced by submerged fermentation of a non-pathogenic strain of *Mucor miehei*), SAVINASE® (produced by submerged fermentation of a genetically modified strain of Bacillus), e.g., the variants disclosed in the International Patent Application published as WO 92/19729, and DURAZYM® (a protein-engineered variant of SAVINASE®). All the above-mentioned commercial proteases are available from Novozymes A/S, DK-2880 Bagsvaerd, Denmark.

Other preferred serine proteases are proteases from Aspergillus, Bacillus such as *Bacillus alcalophilus, Bacillus cereus, Bacillus vulgatus, Bacillus mycoide*, Rhizopus, and subtilins from Bacillus, especially proteases from the species Nocardiopsis such as *Nocardiopsis natto Nocardiopsis dassonvillei* (see, International Patent Application published as WO 88/03947), especially proteases from the species Nocardiopsis sp. NRRL 18262, and *Nocardiopsis dassonvillei* NRRL 18133. Yet other preferred proteases are the serine proteases from mutants of Bacillus subtilisins disclosed in the International Patent Application No. PCT/DK89/00002 and in the International Patent Application published as WO 91/00345, and the proteases disclosed in EP415 296.

Another preferred class of proteases are the metalloproteases of microbial origin. Conventional fermented commercial metalloproteases may be used in the methods of the present invention such as is NEUTRASE® (Zn) (produced by submerged fermentation of a strain of *Bacillus subtilis*), available from Novozymes A/S, DK-2880 Bagsvaerd, Denmark; BACTOSOL® WO and BACTOSOL® SI, available from Sandoz AG, Basle, Switzerland; Toyozyme®, available from Toyo Boseki Co. Ltd., Japan; and PROTEINASE K® (produced by submerged fermentation of a strain of Bacillus sp. KSM-K16), available from Kao Corporation Ltd., Japan.

In another preferred embodiment, the other enzyme is a lipase, especially a microbial lipase. As such, the lipase may be selected from yeast, e.g., Candida; bacteria, e.g., Pseudomonas or Bacillus; or filamentous fungi, e.g., Humicola or Rhizomucor. More specifically, suitable lipases may be the *Rhizomucor miehei* lipase (e.g., prepared as described in EP 238 023), *Thermdmyces lanuginosa* lipase e.g., prepared as described in EP 305 216 (available from Novozymes A/S as LIPOLASE™), Humicola insolens lipase, *Pseudomonas stutzeri* lipase, *Pseudomonas cepacia* lipase, *Candida antarclica* lipase A or B, or lipases from rGPL, *Absidia blakesleena, Absidia corymbifera, Fusarium solani, Fusarium oxysporum, Penicillum cyclopium, Penicillum crustosum, Penicillum expansum, Rhodotorula glutinis, Thiarosporella phaseolina, Rhizopus microsporus, Sporobolomyces shibatanus, Aureobasidium pullulans, Hansenula anomala; Geotricum penicillatum, Lactobacillus curvatus, Brochothrix thermosohata, Coprinus cinerius, Trichoderma harzanium, Trichoderma reesei, Rhizopus japonicus*, or *Pseudomonas plantari*. Other examples of suitable lipases may be variants of any one of the lipases mentioned above, e.g., as described in WO 92/05249 or WO 93/11254.

In another preferred embodiment, the other enzyme is an amylase. Such amylases include Bacillus amylases, e.g., *Bacillus stearothermophilus* amylase, *Bacillus amyloliquefaciens* amylase, *Bacillus subtilis* amylase or *Bacillus licheniformis* amylase (e.g., as available from Novozymes A/S as TERMAMYl®), or Aspergillus amylases, e.g., *Aspergillus niger* or *Aspergillus oryzae* amylase. Other examples of suitable anylases may be variants of any one of the amylases mentioned above, e.g., as described in U.S. Pat. No. 5,093,257, EP 252 666, WO 91/00353, FR 2,676,456, EP 285 123, EP 525 610, or PCT/DK93/00230.

In another preferred embodiment, the other enzyme is a cellulase or cellulolytic enzyme, which refers to an enzyme which catalyses the degradation of cellulose to glucose, cellobiose, triose and other cellooligosaccharides. Preferably, the cellulase is an endoglucanase, more preferably a microbial endoglucanase, especially a bacterial or fungal endoglucanase. Examples of bacterial endoglucanases are endoglucanases obtained from or producible by bacteria from the group of genera consisting of Pseudomonas or Bacillus lautus.

The cellulase or endoglucanase may be an acid, neutral, or alkaline cellulase or endoglucanase, i.e., exhibiting maximum cellulolytic activity in the acid, neutral or alkaline pH range, respectively. Accordingly, a useful cellulase or endoglucanase is an acid cellulase or endoglucanase, preferably a fungal acid cellulase or endoglucanase, more preferably a fungal acid cellulase or endoglucanse enzyme with substantial cellulolytic activity under acidic conditions, which is obtained from or producible by fungi from the group consisting of Trichoderma, Actinomyces, Myrothecium, Aspergillus, and Botrytis.

A preferred acid cellulase or endoglucanase is obtained from the group consisting of *Aspergillus niger, Aspergillus oryzae, Botrytis cinerea, Myrothecium verrucaria, Trichoderma longibrachiatum, Trichoderma reesei*, and *Trichoderma viride*.

Another useful cellulase or endoglucanase is a neutral or alkaline cellulase or endoglucanse, preferably a fungal neutral or alkaline cellulase or endoglucanse, more preferably a fungal alkaline cellulase or endoglucanase with substantial cellulolytic activity under alkaline conditions, which is obtained from fungi selected from the group consisting of Acremonium, Aspergillus, Chaetomium, Cephalosporium, Fusarium, (Cliocladium, Humicola, Irpex, Myceliophthora, Mycogone, Myrothecium, Papulospora, Penicillium, Scopulariopsis, Stachybotrys, and Verticillium.

A preferred alkaline cellulase or endoglucanase is obtained from the group consisting of *Cephalosporium sp., Fusarium oxysporum, Humicola insolens.*, or *Myceliopthora thermophila*, or preferably from the group consisting of *Cephalosporium sp.*, RYM-202, *Fusarium oxysporum*, DSM 2672, *Humicola insolens*, DSM 1800, or *Myceliopthora thermophila*, CBS 117.65.

In another preferred embodiment, the other enzyme is a xylanase such as an endo-1,3-beta-xylosidase (EC 3.2.1.32), xylan 1,4-beta-xylosidase (EC 3.2.1.37), and alpha-L-arabinofuranosidase (EC 3.2.1.55). Preferably the xylanase is obtained from *Aspergillus aculeatus* (an enzyme exhibiting xylanase activity, which enzyme is immunologically reactive with an antibody raised against a purified xylanase derived from *Aspergillus aculeatus* CBS 101.43, see, for example, WO 94/21785); *Aspergillus oryzae* (see, for example, SU 4610007); *Aureobasidium pullulans* (see, for example, EP 0 373 107 A2); *Bacillus circulans* (WO 91/18978); *Bacillus pumilus* (see, for example, WO 92/03540); Bacillus stearothermophilus (see, for example, WO 91/18976, WO 91110724); *Bacillus sp*. AC13 (especially the strain NCIMB 40482, see, for example, WO 94/01532); *Humicola insolens* (see, for example, WO 92/17573); Rhodothermus (see, for example, WO 93/08275); *Streptomyces lividans* (see, for example, WO 93/03155); *Streptomyces viridosporus* (see, for example, EP 496 671 A); *Bacillus licheniformis* (see, for example, JP 9213868);

Thermoascus aurantiacus (see, for example, U.S. Pat. No. 4,966,850); *Trichoderma longibrachiatum* and Chainia sp. (see, for example, EP 0 353 342 A1); *Trichoderma harzianum* and Trichoderma reseei (see, for example, U.S. Pat. No. 4,725,544); *Thermomyces lanuginosus* (see, for example, EP 0 456 033 A2); *Thermomonospora fusca* (see, for example, EP 0 473 545 A2); *Trichoderma longibrachiatum* (see W. J. J. van den Tweel et al., Eds., Stability of Enzymes, Proceedings of an International Symposium held in Maastrich, The Netherlands, 22–25 November 1992, Fisk, R. S. and Simpson, pp.323–328); Dictyoglomus (see, for example, WO 92/18612); Streptomyces (see, for example, U.S. Pat. No. 5,116,746); and/or Thermotoga (see, for example, WO 93/19171). Other examples of suitable xylanases may be variants (derivatives or homologues) of any one of the above-noted enzymes having xylanolytic activity.

In another preferred embodiment, the other enzyme is a pectinase such as a polygalacturonase (EC 3.2.1.15), pectinesterase (EC 3.2. 1.11), or pectin lyase (EC4.2.2. 10). A suitable source organism for pectinases may be *Aspergillus niger*.

In another preferred embodiment, the other enzyme in the acylase composition comprises a hydrolytic enzyme composition produced by a strain of the fungus *Aspergillus aculeatus*, preferably *Aspergillus aculeatus*, CBS 101.43. It is known that this strain produces an enzyme composition comprising pectinolytic and a range of hemicellulolytic enzyme activities.

The other enzyme(s) are present in the acylase composition in an amount from about 0.01 to about 5 mg protein/ml of composition, preferably 0.01 to about 5000 µg protein/ml of composition, and more preferably from about 1 to about 500 µg protein/ml of composition.

The present invention also relates to such compositions for preventing development of a biofilm.

The present invention is further described by the following examples which should not be construed as limiting the scope of the invention.

EXAMPLES

Materials

Chemicals used as buffers and reagents were commercial products of at least reagent grade. Homoserine and homoserine lactone were obtained from Sigma Chemical Co., St. Louis, Mo., while phenylisothiocyanate and amino acid standards were obtained from Pierce, Rockford, Ill. N-butyryl-homoserine and N-octanoyl-homoserine were synthesized according to the procedure described by Eberhard et al., 1981, Biochemistry 20: 2444–2449.

Porcine kidney acylase I was purchased from Sigma Chemical Co., St. Louis, Mo. The acylase has a specific activity of 2350 U/mg; 1 unit (U) of acylase is defined as 17 nmole of N-acetyl-L-methionine deacylated per minute at 25° C. and pH 7.

Biofilm-prone water samples were obtained from a domestic goldfish tank which contains tap water and fish food.

EXAMPLE 1

Amino Acid Analysis

The amount of free amino acid released during deacylation was determined using o-phthaldialdehyde (OPA) in 0.1 M sodium borate pH 11. The assay solution was composed of 10 µl of sample mixed with 40 µl of water and 50 µl of OPA stock solution. The OPA stock solution was made by combining 4 mg of OPA dissolved in 0.1 ml ethanol wth 5 mg of dithiothreitol dissolved in 4.9 ml of 0.1 M sodium borate. The reaction was monitored in 96-well microtiter plate (pathlength ~0.3 cm) at 340 nm by both the final absorption change ($\Delta A$) as well as the initial absorption change rate (v, $\Delta A/min$). Pure homoserine and homoserine lactone (both in the range of 0.05–1 mM) were used to calibrate the assay.

Homoserine (HS) yielded linear correlations of $\Delta A_{340} = 0.451[HS] - 0.006$ ($r^2 = 0.987$) and $v = 1.103[HS] - 0.004$ ($r^2 = 0.989$), while homoserine lactone yielded linear correlations of $\Delta A_{340} = 1.125[HS] + 0.011$ ($r^2 = 0.998$) and $v = 0.682[HS] + 0.005$ ($r^2 = 0.999$). The equations were used to calibrate the OPA-active amine produced from the action of the acylase on N-butyryl-homoserine or N-octanoyl-homoserine (see Example 2).

The identity of the released amino acid was determined by first derivatizing the released amino acids with phenylisothiocyanate (PTC) using the procedure of Henrikson and Meredith, 1984, *Analytical Biochemistry* 136: 65–74, and then submitting the PTC-derivatized amino acids to HPLC analysis using a Hewlett Packard HPLC Model 1050 equipped with a Vydac Protein and Peptide C18 (3×250 mm) reverse-phase column (Vydac, Hesperia, Calif.). Concentrations of homoserine or homoserine lactone to be assayed were in the range of 0.3–3 mM.

Samples were first filtered using a Microcon-3 with a molecular weight cut-off of 3 kDa (Amicon, Inc., Beverly, Mass.) to separate large proteins (acylase). The filtrates were then dried using a Savant AS160 Speed-Vac (Savant Instruments, Inc., Farmingdale, Conn.) and resuspended twice in 100 µl of coupling buffer composed of acetylnitrile, pyridine, triethylamine, and water 10:5:2:3 v/v/v. After adding 3 µl of phenylisothiocyanate, samples were incubated at 23° C. for 10 minutes, then dried and resuspended in 50% aqueous acetonitrile, and redried. The resulting samples were dissolved in 50 mM ammonium acetate pH 6 (Buffer A). The treated samples containing 6–60 nmoles of PTC-derivatized homoserine were analyzed by HPLC as described above. The amino acids were eluted with Buffer A and Buffer B composed of 0.1 M ammonium acetate pH 6, acetylnitrile, and methanol mixed in the ratio of 46/44/10 v/v/v, according to the following elution profile:

| Time, min | Buffer A, % | Buffer B, % |
| --- | --- | --- |
| 0 | 0 | 100 |
| 15 | 15 | 85 |
| 30 | 50 | 50 |
| 34 | 100 | 0 |
| 37 | 100 | 0 |
| 40 | 0 | 100 |
| 50 | 0 | 100 |

Homoserine and homoserine lactone yielded a PTC-derivative with the same HPLC retention time of 13.7 minutes. Apparently, the derivatization hydrolyzed homoserine lactone to homoserine. In comparison, the PTC-derivatives of serine and threonine had a retention time of 12.2 and 16.8 min, respectively. No major HPLC peak was detected for samples that contained only either N-acyl-homoserine lactone, or acylase (native or heat-inactivated), or N-acyl-homoserine lactone plus heat-inactivated acylase.

EXAMPLE 2

Deacylation of N-acyl-homoserine by Porcine Kidney Acylase I

N-butyryl-homoserine was deacylated with acylase by reacting 5–50 mM N-butyryl-homoserine with 240–2400 U of acylase (specific activity=2350 U/mg) per ml of 90 mM sodium phosphate pH 7 at 23° C. N-octanoyl-homoserine was deacylated with acylase by reacting 5 mM N-octanoyl-homoserine (diluted from 0.1 M stock solution made in dimethylformamide) with 470 U of acylase per ml of 90 mM sodium phosphate pH 7 and 10% DMF at 23° C. The reactions were performed in a 96-well microtiter plate and sampled periodically for amino acid analysis as described in Example 1. Solutions that contained N-acyl-homoserine alone, acylase alone, and N-acyl-homoserine plus heat-inactivated acylase (15 minutes at 100° C.) served as controls. Spectral data were recorded using a Molecular Devices Spectra Max 340 microtiter plate reader (Molecular Devices, Sunnyvale, Calif.) in 96-well microtiter plate.

Deacylation of N-butyryl-homoserine or N-octanoyl-homoserine with acylase produced OPA-active amine, indicating the deacylation of both compounds. Because fitting the observed v and $\Delta A_{340}$ to the calibration equations of homoserine yielded similar OPA-active amine concentrations (variation <10%), while fitting to the calibration equations of homoserine lactone yielded very different OPA-active amine concentrations (variation ~4 to 5-fold), the produced OPA-active amine was most likely homoserine (rather than homoserine lactone).

The product identity of the enzymatic reaction was verified by amino acid analysis as described in Example 1. The reacted solutions yielded a compound whose PTC-derivative had a HPLC peak essentially identical to that observed for homoserine or homoserine lactone. Based on the calibration of homoserine, the concentration of phenylisothiocyanate-active amine from the solutions was found to be close to the concentration of OPA-active amine (variation <15%), indicating that homoserine was the major (if not sole) product of the enzymatic reaction.

When the initial concentration of N-butyryl-homoserine and N-octanoyl-homoserine were both 5 mM, the latter was deacylated by acylase (470 U/ml) with a rate six-fold slower than that of N-butyryl-homoserine. At 2400 U/ml level, acylase deacylated N-butyryl-homoserine with a rate proportional to the initial concentration of N-butyryl-homoserine in the range of 10–150 mM, indicating a $K_m \geq 150$ mM. With 150 mM N-butyryl-homoserine, an initial reaction rate of 6 pmole/min/U or 15 nmole/min/mg of acylase was observed.

EXAMPLE 3

Effect of Acylase on Aquatic Microbial Growth

Water samples of 1 ml, free of visually detectable insolubles, were taken on different days from a one gallon fish-tank and aliquoted into 1.5-ml methacrylate cuvettes for three series of experiments. Spectral data were recorded using a Shimadzu UV-visible spectrophotometer Model UV160U (Shimadzu, Pleasanton, Calif.).

For series A, 0, 1.4, 14, or 150 μg of native acylase (specific activity=2350 U/mg) or heat-inactivated acylase were added to the 1 ml water samples.

For series B, 0, 0.41, 4.1, or 45 μg of native acylase (specific activity=8700 U/mg) were added to the 1 ml water samples, while glass-distilled water with or without 50 μg acylase served as controls. The cuvettes were capped and incubated (without shaking/stirring) for up to 18 days at 23° C. At day 0, 5, 11, 14, or 18, the solutions were subjected to a spectral scan from 1000–300 nm. For series A, the solutions were first stirred and, after the 1000-nm absorption $A_{1000}$ stabilized, subjected to the scan. The abundance of microbial particles (or turbidity) was measured at $A_{300}$.

For series C, 0, 1.5, or 15 μg of native acylase (specific activity=2350 U/mg) or heat-inactivated acylase were added to the 1 ml water samples, while glass-distilled water with 0, 15, or 150 μg acylase/ml served as control.

The incubations were carried out in polystyrene 96-well microtiter plate. At selected time points, 25 μl of 1% crystal violet (Aldrich Chemical Co., Milwaukee, Wis.; 95% purity) was added to each well and incubated for 15 minutes. Then the dye solution was discarded, and the well was rinsed five times with 0.2 ml of distilled water. Two-hundred μl of ethanol (96%) was added to dissolve the crystal violet adsorbed by biofilm that grew on the polystyrene surface, and 125 μl of the ethanol solution was transferred to another 96-well microtiter plate and the absorption at 600 nm was measured using a Molecular Devices microtiter plate reader. This method was adapted from the procedure of O'Toole and Kolter, 1998, *Mol. Microbiol.* 28: 449–461.

The results of the series A experiments are summarized in Table 1 with regard to the microbial growth-induced $A_3$00 change, as a function of the state and dosage of acylase, in the fish-tank water sample.

TABLE 1

Effect of acylase I on aquatic microbial growth (series A).

| Acylase, μg/ml | | Incubation time, day | | | |
|---|---|---|---|---|---|
| Native | Inactive | 0 | 5 | 11 | 18 |
| 0 | 0 | 0.031 ± 0.001 | 0.031 ± 0.001 | 0.054 ± 0.008 | 0.074 ± 0.013 |
| 1.4 | 0 | 0.033 ± 0.001 | 0.034 ± 0.001 | 0.051 ± 0.001 | 0.067 ± 0.003 |
| 0 | 1.4 | 0.037 ± 0.001 | 0.037 ± 0.001 | 0.052 ± 0.002 | 0.068 ± 0.002 |
| 14 | 0 | 0.041 ± 0.001 | 0.044 ± 0.001 | 0.052 ± 0.002 | 0.081 ± 0.001 |
| 0 | 14 | 0.061 ± 0.001 | 0.048 ± 0.001 | 0.058 ± 0.001 | 0.082 ± 0.003 |
| 150 | 0 | 0.055 ± 0.001 | 0.172 ± 0.013 | 0.100 ± 0.001 | 0.107 ± 0.011 |
| 0 | 150 | 0.310 ± 0.015 | 0.243 ± 0.005 | 0.131 ± 0.011 | 0.149 ± 0.016 |

When the incubations were started, the solutions containing 14 or 150 μg/ml native acylase (specific activity=2350 U/mg) showed $A_3$00 slightly higher than that of the water sample, attributable to the absorption of the added protein. The solutions containing heat-inactivated acylase had an even higher $A_{300}$ (Table 1, day 0), due to the turbidity caused by the aggregation/precipitation of acylase made during the heat-inactivation.

As judged by the $A_{300}$ change of the water sample to which neither native nor inactivated acylase was added, microbial growth in the incubating cuvette became detectable after days of incubation (FIG. 1). From day 11 to day 18, the microbial growth resulted in an $A_{300}$ increase of 0.02. During the same time, the $A_{300}$ increase in solutions containing 1.4 μg/ml of native or inactivated acylase was 0.016 or 0.016, respectively, and the $A_{300}$ increase in solutions containing 14 μg/ml native or inactivated acylase was 0.029 or 0.024, respectively. For solutions containing 150 μg/ml native or inactivated acylase, the $A_{300}$ increase at the same time period was 0.007 or 0.018, respectively. It appeared that adding acylase at 150 μg/ml led to an approximately 60% reduction in the microbial growth during the 7-day incubation (from day 11 to day 18), in comparison with solutions having either 0 or 150 μg/ml inactive acylase.

TABLE 2

Effect of acylase I on aquatic microbial growth (series B).

| Acylase μg/ml | Incubation time, day | | | |
|---|---|---|---|---|
| | 0 | 5 | 11 | 14 |
| 0 | 0.001 ± 0.001 | 0.015 ± 0.002 | 0.023 ± 0.004 | 0.049 ± 0.004 |
| 0.41 | 0.006 ± 0.001 | 0.019 ± 0.001 | 0.018 ± 0.001 | 0.027 ± 0.005 |
| 4.1 | 0.003 ± 0.001 | 0.017 ± 0.001 | 0.012 ± 0.002 | 0.021 ± 0.004 |
| 45 | 0.011 ± 0.001 | 0.033 ± 0.003 | 0.029 ± 0.002 | 0.052 ± 0.004 |
| 0* | 0.000 ± 0.001 | 0.004 ± 0.002 | 0.002 ± 0.001 | 0.010 ± 0.004 |
| 45* | 0.010 ± 0.001 | 0.019 ± 0.002 | 0.013 ± 0.001 | 0.035 ± 0.004 |

*In glass-distilled water

The results of the series B experiments are summarized in Table 2 with regard to the microbial growth-induced $A_{300}$ change, as function of acylase dosage, in the selected fish-tank water sample. Because the solutions were not stirred/resuspended, the $A_{300}$ reading reflected the biofilm formation on the inside wall-surface of the cuvettes, rather than the overall microbial growth as measured in series A.

Figure 2:
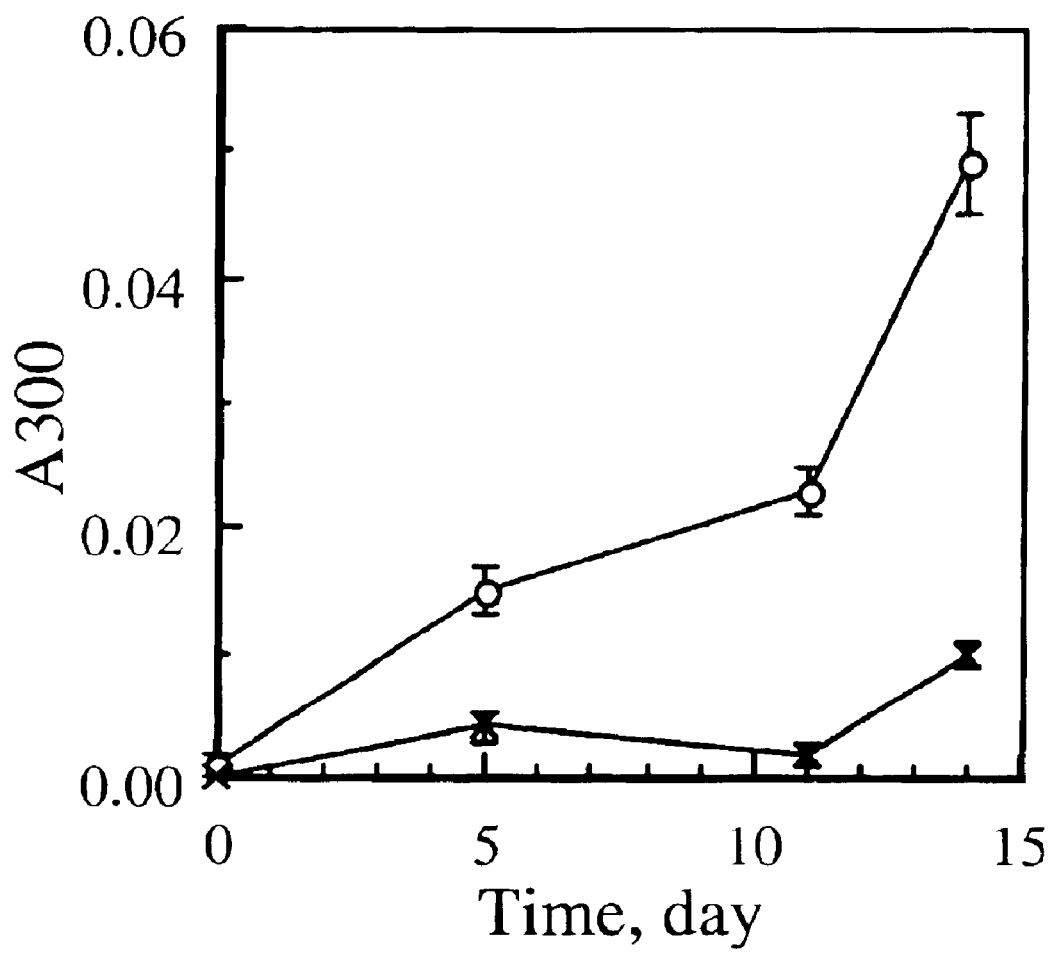
FIG. 2 shows microbial growth-caused absorption change at 300 nm as function of incubation time. No acylase was added to either fish-tank (o) or distilled (x) water sample.

As shown in FIG. 2, significant microbial growth occurred in fish-tank water (o), in comparison to distilled water (x), during incubation. Because native acylase (specific activity=8700 U/mg) at 45 μg/ml dose had detectable $A_{300}$, the difference $\Delta A_{300}$ between acylase-containing fish-tank water and acylase-containing distilled water reflected the microbial growth-caused $A_{300}$ change in the former solution. No significant effect of 45 μg/ml acylase was seen for the first 11 days. However, the acylase apparently made a ~65% reduction in microbial growth-associated $A_{300}$ at day 14. Detectable reduction in $A_{300}$ (~45 or ~57%) was also observed when acylase was dosed at 0.41 or 4.1 μg/ml level.

The results of the series A experiments are summarized in Table3 measuring crystal violet adsorption on polystyrene surface. In distilled water, no crystal violet was adsorbed with or without the presence of acylase (native or inactivated). In the fish-tank water, however, the container's wall could be stained to purple color, indicating the dye adsorption by the microbial biofilm formed on the wall surface. Quantitated by the redissolved crystal violet in ethanol (which generated a purple solution), the presence of 150 μg/ml acylase seemed to reduce the biofilm formation by 10%, in comparison to solutions having either no or inactivated acylase.

TABLE 3

Effect of acylase I (series C). Release of biofilm-adsorbed crystal violet ($A_{600}$†) as function of acylase concentration and time.

| Acylase, μg/ml | | Incubation time, h | |
|---|---|---|---|
| Native | Inactive | 1 | 22 |
| 0 | 0 | 0.021 ± 0.001 | 0.032 ± 0.002 |
| 15 | 0 | 0.018 ± 0.001 | 0.028 ± 0.001 |
| 0 | 15 | 0.020 ± 0.001 | 0.037 ± 0.001 |
| 150 | 0 | 0.013 ± 0.001 | 0.023 ± 0.001 |
| 0 | 150 | 0.026 ± 0.001 | 0.033 ± 0.001 |
| 0* | 0* | 0.003 ± 0.001 | −0.004 ± 0.001 |
| 15* | 0* | −0.004 ± 0.001 | −0.006 ± 0.001 |
| 0* | 15* | 0.001 ± 0.001 | −0.006 ± 0.001 |
| 150* | 0* | −0.004 ± 0.001 | −0.006 ± 0.001 |
| 0* | 150* | 0.001 ± 0.001 | −0.008 ± 0.001 |

†Difference between measured $A_{600}$ and 0.069 (observed for 96-well microtiter plate plus 125 μl ethanol, ±0.007).
*In glass-distilled water.

Example 4

Analysis of Biofilm Sample

The biofilm sample, on which acylase showed a potential biofilm-preventing activity, was analyzed by Microbe Inotech in St. Louis, Mo. Two major bacterial strains were isolated and initially identified as *Pseudomonas pseudoalcaligenes* (or *P. oleovorans*) and *Microbacterium imperiale* by the first 500 bp sequence of their 16S rRNA. Pseudomonas bacteria are known to use N-acylhomoserine lactones as the biofilm-regulating signals.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for removing biofilm on a surface, comprising contacting the surface with an effective amount of one or more E.C. 3.5.1 acylases and a carrier to degrade a lactone produced by one or more microorganisms, wherein the degradation of the lactone removes the biofilm.

2. The method of claim 1, wherein the lactone is a homoserine lactone.

3. The method of claim 2, wherein the homoserine lactone is an N-acyl-L-homoserine lactone.

4. The method of claim 3, wherein the N-acyl-L-homoserine lactone is N-(3-oxododecanoyl)-L-homoserine lactone.

5. The method of claim 3, wherein the N-acyl-L-homoserine lactone is N-butyryl-L-homoserine lactone.

6. The method of claim 1, wherein the biofilm is comprised of one or more microorganisms selected from the group consisting of an aerobic bacterium, anaerobic bacterium, fungus, algae, and protozoan.

7. The method of claim 6, wherein the aerobic bacterium is an Aeromonas, Burkholdena, *Escherichia coli*, Flavobacterium, Micobocterium, Pseudomonas, Salmonella, or Staphylococcus strain.

8. The method of claim, 6, wherein the anaerobic bacterium is a Desulfovibrio strain.

9. The method of claim 6, wherein the fungus is a yeast or filamentous fungus.

10. The method of claim 9, wherein the yeast is a Candida strain.

11. The method of claim 1, wherein the surface is a hard, soft, or porous surface.

12. The method of claim 1, wherein the acylase is obtained from a plant, animal, or microbial source.

13. The method of claim 12, wherein the microbial source is a bacterial or fungal source.

14. The method of claim 13, wherein the bacterial source is an Acetobacter, Acinetobacter, Agrobacterium, Alcaligenes, Arthrobacter, Azobtobacter, Bacilius, Comamonas, Clostridium, Gluconobacter, Halobacterium, Mycobacterium, Rhizobium, Salmonella, serratia, Streptomyces, E. coli, Pseudomonas, Wolinella, or methylotrophic bacterium strain.

15. The method of claim 13, wherein the fungal source is a yeast or filamentous fungus.

16. The method of claim 15, wherein the yeast source is a Candida, Kluyveromyces, Pichia, Saccharomyces, Schizosaccharomyces, or Yarrowia strain.

17. The method of claim 15, wherein the filamentous fungal source is an Acremonium, Aspergillus, Aureobasidium, Chrysosporium, Cryptoclccus, Filibasidium, Fusarium, Humicola, Magnaporthe, Monilia, Mucor, Myceliophthora, Neocallimastix, Neurospora, Paecilomyces, Penicillium, Phanerochaete, Piromyces, Schizophyllum, Sclerotium, Sporotrichum, Talaromyces, Thermoascus, Thielavia, Tolypocladium, or Trichoderma strain.

18. The method of claim 1, wherein the effective concentration of the one or more acylases is about 0.001 to about 1 g of acylase per kilogram of water.

19. The method of claim 18, wherein the effective concentration of the one or more acylases is about 0.01 to about 1 g of acrylase per kilogram of water.

20. The method of claim 19, wherein the effective concentration of the one or more acylases is about 0.01 to about 0.5 g of acylase per kilogram of water.

21. The method of claim 20, wherein the effective concentration of the one or more acylases is about 0.01 to about 0.1 g of acylase per kilogram of water.

22. The method of claim 1, wherein the one or more acylases have a pH optimum in the range of about 3 to about 10.

23. The method of claim 22, wherein the one or more acylases have a pH optimum in the range of about 4 to about 9.

24. The method of claim 23, wherein the one or more acylases have a pH optimum in the range of about 5 to about 8.

25. The method of claims 1, wherein the one or more acylases have a temperature optimum in the range of about 5° C. to about 100° C.

26. The method of claim 25, wherein the one or more acylases have a temperature optimum in the range of 25° C. to about 75° C.

27. The method of claim 26, wherein the one or more acylases have a temperature optimum in the range of about 25° C. to about 50° C.

28. The method of claim 1, wherein the contacting the surface with the effective amount of the one or more E.C. 3.5.1 acylases and the carrier further comprises one or more agents selected from the group consisting of dispersants, surfactants, detergents, enzymes other than the one or more acylases, anti-microbials, and biocides.

29. The method of claim 28, wherein the enzymes other than the one or more acylases are selected from the group consisting of an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galatosidase, glucoamylase, alpha-glucosidase, beta-glucosidase, haloperoxidase, invertase, laccase, lipase, mannosidase, oxidase, pectinase, pepticioglutaminase, peroxidase, phytase, polyphenoloxidase, protease, ribonuclease, transglutaminase, or xylanase.

* * * * *